United States Patent [19]

Kaminski et al.

[11] Patent Number: 5,648,360

[45] Date of Patent: Jul. 15, 1997

[54] PENTACYCLIC ANTIHISTAMINES

[75] Inventors: James J. Kaminski, Long Valley; Shing-Chun C. Wong, Union; Nicholas I. Carruthers, North Plainfield, all of N.J.

[73] Assignee: Schering Corporation, Kenilworth, N.J.

[21] Appl. No.: 335,885

[22] PCT Filed: May 17, 1993

[86] PCT No.: PCT/US93/04456

§ 371 Date: Nov. 14, 1994

§ 102(e) Date: Nov. 14, 1994

[87] PCT Pub. No.: WO93/23400

PCT Pub. Date: Nov. 25, 1993

Related U.S. Application Data

[63] Continuation-in-part of Ser. No. 885,429, May 19, 1992, abandoned.

[51] Int. Cl.[6] .................................................. A61K 31/47
[52] U.S. Cl. ........................... 514/80; 546/49; 546/56
[58] Field of Search ........................... 514/280; 546/49, 546/56

[56] References Cited

U.S. PATENT DOCUMENTS

| | | |
|---|---|---|
| 3,326,924 | 6/1967 | Villani . |
| 4,731,447 | 3/1988 | Schumacher et al. ............. 546/93 |
| 4,826,853 | 5/1989 | Piwinski et al. ............. 514/298 |
| 5,089,496 | 2/1992 | Piwinski ............. 514/253 |
| 5,151,423 | 9/1992 | Piwinski et al. ............. 514/254 |

FOREIGN PATENT DOCUMENTS

| | | |
|---|---|---|
| 0 396 083 | 11/1990 | European Pat. Off. . |
| 93-23400 | 11/1993 | WIPO . |

OTHER PUBLICATIONS

Merck Index, 10th Edition, Rahuay, NJ, 1983 page on R33.

*Primary Examiner*—Donald G. Daus
*Attorney, Agent, or Firm*—Henry C. Jeanette

[57] ABSTRACT

Disclosed are novel compounds having structural formula (I)

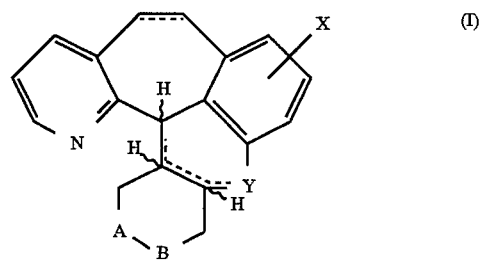

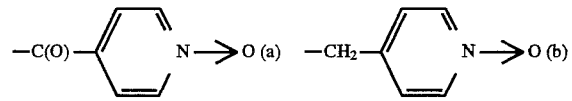

or a pharmaceutically acceptable salt thereof, wherein X is hydrogen, halo, —$CF_3$ or lower alkyl; Y is —$(CH_2)_n$—, wherein n is 0, 1, 2 or 3, —C(O)—, —$CH_2C(O)$—, —$CH_2CH_2C(O)$— or —CH(OH)—; A is —N(R)— and B is —$CH_2$—, or A is —$CH_2$— and B is —N(R)—; R is hydrogen, lower alkyl, lower alkanoyl, —$CO_2R^1$, (a) or (b); $R^1$ is hydrogen, lower alkyl or —$CH_2CCl_3$; and - - - - represents an optional double bond, with the proviso that the ring containing Y has only one optional double bond. Also disclosed are pharmaceutical compositions comprising these compounds and their use in treating allergy and inflammation.

11 Claims, No Drawings

PENTACYCLIC ANTIHISTAMINES

The present application is the United States national application corresponding to International Application No. PCT/US93/04456, filed May 17, 1993 and designating the United States, which PCT application is in turn a continuation-in-part of U.S. application Ser. No. 07/885,429, filed May 19, 1992 now abandoned, the benefit of which applications are claimed pursuant to the provisions of 35 U.S.C. 120, 363 and 365 (C).

BACKGROUND OF THE INVENTION

The present invention mimes to pentacyclic compounds, pharmaceutical compositions comprising such compounds, and to their use as antihistamines and as platelet-activating factor (PAF) antagonists.

SUMMARY OF THE INVENTION

Novel compounds of the present invention are represented by the structural formula I:

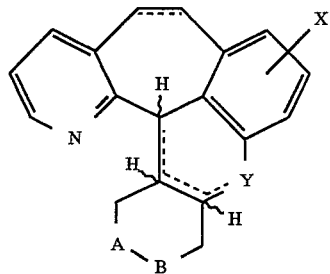

I or a pharmaceutically acceptable salt thereof, wherein:

X is hydrogen, halo, —$CF_3$ or lower alkyl with hydrogen, halo, —$CF_3$ or —$CH_3$ being preferred, the phenyl ring contains 1,2, or 3 X substituents and when there are 2 or 3 X substituents said substituents are the same or different;

Y is —$(CH_2)_n$—, wherein n is 0, 1, 2 or 3, —C(O)—, —$CH_2C(O)$—, —$CH_2CH_2C(O)$— or —CH(OH)—;

A is —N(R)— and B is —$CH_2$—, or A is —$CH_2$— and B is —N(R)—;

R is hydrogen, lower alkyl, lower alkanoyl, —$CO_2R^1$,

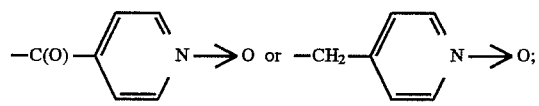

$R^1$ is hydrogen, lower alkyl or —$CH_2CCl_3$; and

- - - - represents an optional double bond, with the proviso that the ring containing Y has only one optional double bond—i.e., when present, there can only be one double bond in the ring containing Y.

Compounds represented by formula I include compounds of the formula:

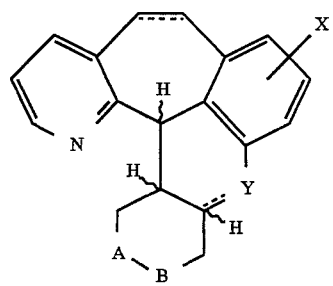

Iii wherein X, Y, A, B and the dotted line - - - are as defined for formula I above.

Compounds represented by formula I also include compounds of the formula:

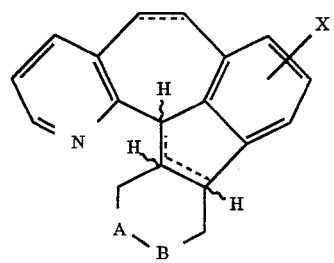

Iii wherein X, A, B and the dotted line - - - are as defined for formula I above.

Compounds represented by formula Iii include compounds of formula XIV:

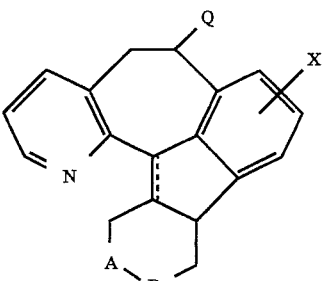

XIV wherein Q is =O or —OH, and X, A, B and the dotted line - - - are as defined for formula I.

Preferred compounds of the invention are those wherein Y is —$(CH_2)_n$— wherein n is 1, —C(O)— or =CH— (i.e., wherein Y is —$(CH_2)_n$—, n is 1 and the optional adjacent double bond is present). Another group of preferred compounds is that wherein A is —$CH_2$— and B is —N(R)—. Also preferred are compounds wherein X is halo, more preferably chloro. Preferred values for R are lower alkyl, especially methyl; acetyl; ethyl carboxylate; and pyridylcarbonyl N-oxide.

Especially preferred are compounds of formula I wherein X is chloro, Y is —$CH_2$—, —C(O)— or =CH—, A is —$CH_2$—, B is —N(R)— and R is methyl, acetyl, ethylcarboxylate or pyridylcarbonyl N-oxide.

The invention also includes a pharmaceutical composition which comprises a compound of formula I in combination with a pharmaceutically acceptable carrier.

The invention further includes a method of treating allergy or inflammation in a mammal which comprises administering an effective amount of a compound of formula I to a mammal in need of such treatment.

DETAILED DESCRIPTION

As used herein, the term "lower alkyl" means straight or branched carbon chains of 1 to 6 carbon atoms.

"Halo" refers to fluoro, chloro, bromo or iodo.

"Lower alkanoyl" refers to lower alkyl carbonyl radicals wherein lower alkyl is as defined above.

When Y is —CH$_2$(CO)— or —CH$_2$CH$_2$C(O)—, the methylene group is attached to the piperidino-ring portion of the molecule and the carbonyl group is attached to the phenyl-ring portion.

Compounds of the invention may exist in isomeric forms. Due to the possible presence of several chiral centers, various enantiomers and/or diastereomers can be present. All such isomers are contemplated as being part of this invention, both in pure form and in admixture, including racemic mixtures.

The compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

The phenyl ring in the structure of formula I may contain one, two or three X substituents. In compounds where there is more than one such substituent, they may be the same or different. Thus, compounds having combinations of such substituents are within the scope of the invention. Also, the line drawn into the ring from the X group indicates that such group or groups can be attached at any of the available positions, i.e. the 7, 8 and/or 9 positions.

Certain compounds of the invention will be acidic in nature, e.g., those compounds which possess a carboxyl or phenolic hydroxyl group. These compounds may form pharmaceutically acceptable salts. Examples of such salts may include sodium, potassium, calcium, copper, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts and quaternary ammonium salts. For example, the pyrido-nitrogen atoms may form salts with strong acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The quaternary ammonium salts are prepared by conventional methods, e.g., by reaction of a tertiary amino group in a compound of formula I with a quaternizing compound such as an alkyl iodide, etc. The free base forms differ from their respective salt forms somewhat in certain physical properties, such as solubility in polar solvents, but the salts are otherwise equivalent to their respective free base forms for purpose of the invention.

All such acid, base and quaternary salts are intended to be pharmaceutically acceptable salts within the scope of the invention and all acid and base salts are considered equivalent to the free forms of the corresponding compounds for purposes of the invention.

Compounds of formula I can be prepared by methods well known in the art using starting materials known in the art or readily prepared by methods well known in the art.

For example, compounds of formula Ia, wherein Y is —C(O)— and A, B and X are as defined above, are prepared by cyclization of compounds of formula II, wherein A, B and X are as defined above and R$^{10}$ is, for example, lower alkyl, especially methyl or ethyl:

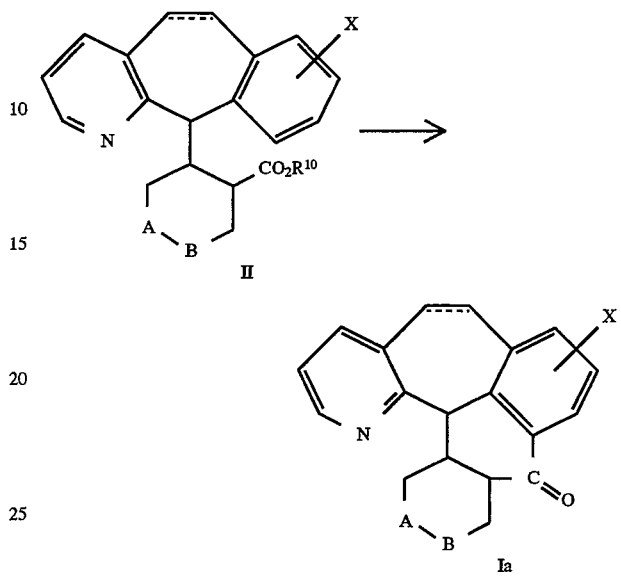

The reaction is carried out at room temperature in a solvent such as ethanol using a base such as KOH, followed by reaction at elevated temperature with a strong acid such as triflic acid.

Starting compounds of formula II wherein X, A and B are as defined above and R is —CH$_3$, i.e. IIa, are prepared, for example, by reaction of a compound of formula III with a compound of formula IV (wherein R$^{10}$, A and B are as defined above and R is —CH$_3$) in the presence of sodium amide in an inert solvent such as tetrahydrofuran:

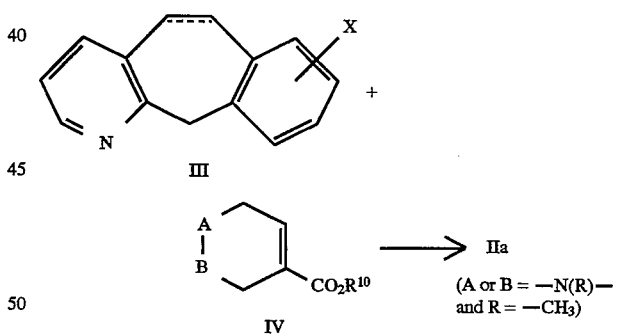

A compound of formula IIa can be reacted with 2,2,2-trichloroethyl-chloroformate in an inert solvent in the presence of a base, then reacted with zinc in acetic acid followed by acetic anhydride to obtain a corresponding compound of formula II wherein X, A and B are as defined above and R is acetyl.

A compound of formula III is readily available by reduction of azaketones of formula IIIa. Reduction of the ketone function of IIIa may be achieved directly via the Wolff-Kishner or Clemmensen reactions, or stepwise. Thus, compounds of formula IIIa may be first reduced to the corresponding alcohols using sodium borohydride, and the alcohols converted to the corresponding chlorides using thionyl chloride with the halogen being removed using zinc in acetic acid. Methods and synthetic schemes for the preparation of azaketones of formula IIIa are disclosed in U.S. Pat. Nos. 3,326,924 and 4,731,447.

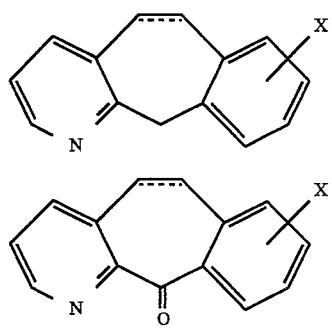

Alternatively, compounds of formula I wherein A is —CH$_2$—, B is —N(R)— and R is CH$_3$, i.e., compounds of formula Ib, are prepared by cyclization of the corresponding compound of formula IIa by treatment with acid at elevated temperatures:

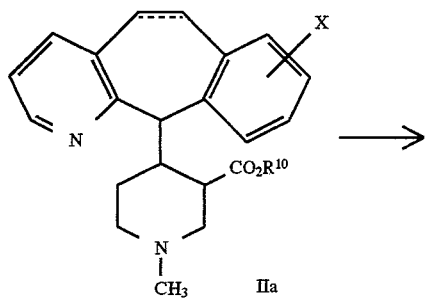

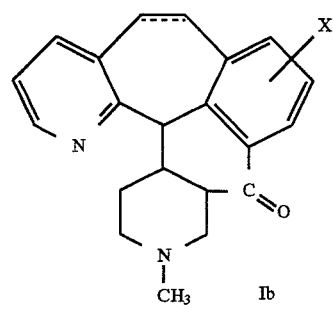

Compounds of formula I wherein Y is —(CH$_2$)$_n$C(O)—, n=1 or 2, and A, B and X are as defined above, i.e., compounds of formula Ic and Ic', are prepared by cyclization of compounds of formula V or Va, wherein R$^{10}$ is as defined above, e.g., lower alkyl, especially methyl or ethyl:

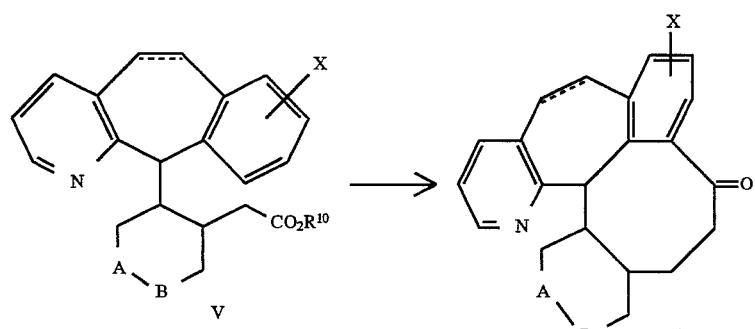

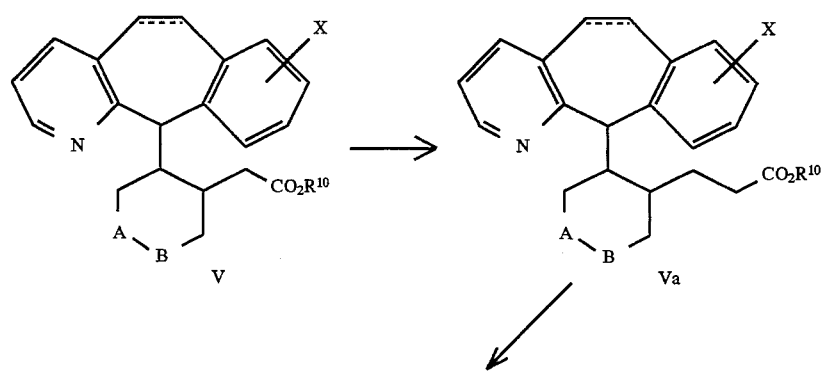

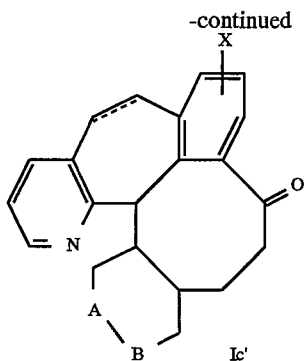

The reaction is carried preparation out at room temperature in a solvent such as ethanol using a base such as KOH, followed by reaction at elevated temperature with a strong acid such as triflic acid.

Starting compounds of formula V are prepared, for example, from compounds of formula II via standard methods of carboxylic ester homologation. For example, II is converted to the corresponding carboxylic acid, which may then be converted to the acid chloride. Compound V can be obtained by the well-known Arndt-Eistert reaction: the acid chloride is first treated with diazomethane to give a diazoketone, then the diazoketone is treated with a silver salt, e.g. silver oxide or silver benzoate, in the presence of an amine such as triethylamine and an alcohol $R^{10}OH$, wherein $R^{10}$ is as described above. Alternatively, the diazoketone can be subjected to photolysis in the presence of an alcohol $R^{10}OH$ to obtain a compound of formula V. By repeating this homologation sequence compound Va can be obtained from compound V.

Compounds of formula Id, wherein Y is —$(CH_2)_n$— and n is 0, and wherein A,B, and X are as defined above, are prepared from starting materials of formula VI according to the following reaction scheme:

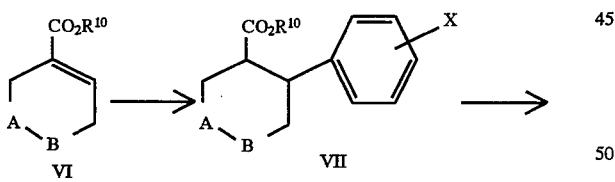

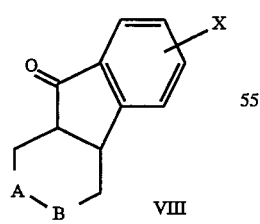

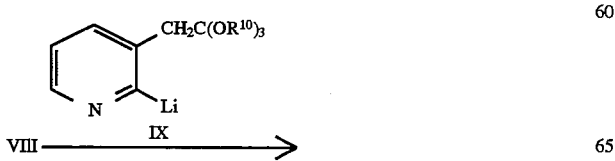

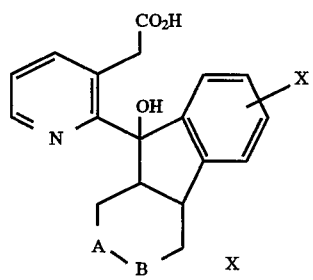

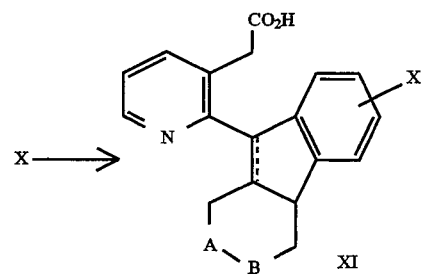

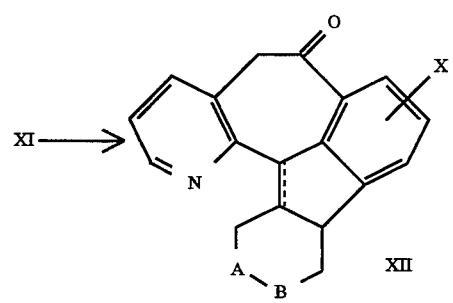

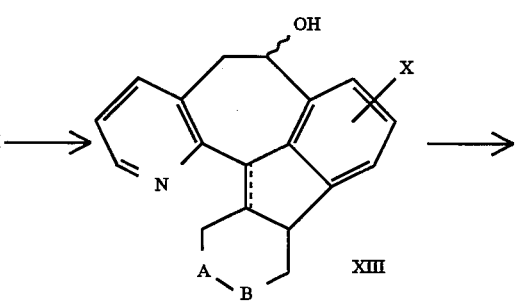

-continued

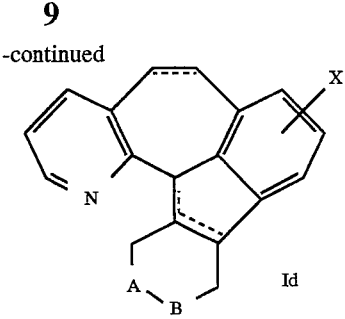

Id

Reaction of VI with a Grignard reagent in the presence of cerium chloride can provide VII, which upon treatment with aqueous base followed by strong acid gives VIII. Addition of lithiated pyridine, IX, to VIII affords alcohol X, which can be reduced or dehydrated to obtain compounds XI. Treatment of XI with strong acid affords XII, which can be reduced to provide XIII. Alcohol XIII can be reduced or dehydrated to yield compounds Id.

Preparation of compounds of formula I in which the cycloheptane ring is unsaturated, i.e.—a cycloheptene ring, formula Ie wherein n is 0 or 1, and A, B, X and the dotted line - - - - are as defined for formula I.

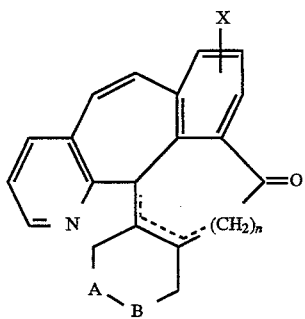

The ketone is converted to the alcohol (NaBH$_4$) and the alcohol is converted to a sulfonate (methanesulfonyl chloride/pyridine, p-tosylchloride/pyridine or triflurometh-ylsulfonyl chloride/pyridine) which is reduced using lithium aluminium hydride. Alternatively, the alcohol may be converted to a halide using thionyl chloride, and the halide removed using zinc in acetic acid. Additional methods include the direct reduction of the ketone via the Wolff-Kishner or Clemmensen procedures. These methods all leave the cycloheptene double bond intact.

Compound XII is converted to XIII via sodium borohydride reduction and the conversion of XIII to Id wherein Id contains a cycloheptene ring is accomplished using standard dehydration methods. For example, using mineral acids (H$_2$SO$_4$), sulfonic acids (p-TsOH, CF$_3$SO$_3$H ClSO$_3$H) or via elimination of the corresponding sulfonate derivative of XIII under basic conditions (e.g., triethylamine, DMAP (4-dimethylaminopyridine), DBU (diazabicyclo-[5.4.0] undec-7-ene, DBN (diazabicyclo[4.3.0]non-5-ene)).

In cases wherein compounds of formula Id contain a cycloheptane ring, the keto group of compound XII or the alcohol group of compound XIII may be readily removed using the methods already described for the removal of the ketone functionality from compounds of formula Ic.

Compounds of formula I can be converted to other compounds of formula I using various conventional procedures. For example, ketones of formula Ia can be reduced to compounds wherein Y is —CH(OH)—, for example by reaction with sodium borohydride, and compounds wherein Y is —CH(OH)— can be dehydrated by heating in the presence of an acid to form a compound wherein Y is —(CH$_2$)$_n$—, n is 1 and the optional adjacent double bond is present (i.e., Y is =CH—). The resultant unsaturated ring can undergo hydrogenation to provide a compound of formula Ia wherein Y is —CH$_2$—. Compounds of formula Ib wherein R is —CH$_3$ can similarly be converted from the ketone (Y is —C(O)—) to the alcohol (Y is —C,H(OH)—) to the unsaturated compound (Y is =CH—) to the saturated analog (Y is —CH$_2$—). Similarly, compounds of formula Ic can be reduced, dehydrated and hydrogenated to the corresponding saturated compound of formula I; compounds of formula I wherein Y is propyl can be prepared by analogous methods.

Compounds of formula I wherein Y is —CH$_2$— and R is —CH$_3$ can be converted to the carbamate (e.g., R is —CO$_2$CH$_2$CH$_3$) using lower alkyl chloroformate in the presence of a base, or can be converted to the piperidino analog (i.e., R is H) by treating with a reagent such as 2,2,2-trichloroethyl chloroformate in the presence of a base, followed by reaction with zinc in acetic acid. Compounds of formula I, wherein A is —CH$_2$—, B is —N(R)— and R is H, can be converted to the pyridylcarbonyl N-oxides by reaction with iso-nicotinic acid-N-oxide in the presence of coupling agents such as hydroxybenzotriazole and 1-(3-dimethylamino-propyl)-3-ethyl carbodiimide HCl. A piperidino compound of formula I as defined immediately above can be converted to the pyridylmethyl N-oxide by reaction with a pyridyl reagent of the formula

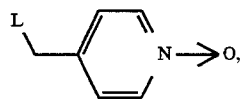

wherein L is a leaving group such as mesyl, tosyl, or bromo, in the presence of a base such as pyridine or triethylamine; the reaction is carried out in an inert solvent, usually at reflux temperature.

Compounds of formula I containing an optional double bond in the Y containing ring may be isomerized to other double bond isomers. Treating the olefin product with suitable catalysts, such as palladium, platinum, Raney nickel and/or rhodium and the like, in a suitable protic solvent, e.g., C$_1$ to C$_{12}$ alcohols, at ambient temperature to heating under reflux, may result in isomeric olefin products. These product mixtures may be separated into their individual components chromatographically using techniques known to those skilled in the art.

It is contemplated that intermediates XII and XIII described above in the preparation of compounds of formula Id will have antihistaminic and PAF antagonistic activity. Therefore, compounds having the following structural formula XIV represent another aspect of this invention:

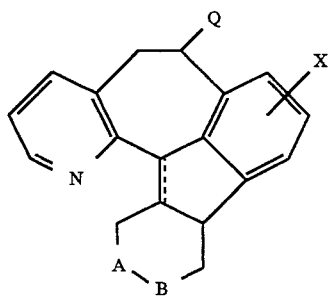

or a pharmaceutically acceptable salt thereof, wherein:

X is hydrogen, halo, —CF$_3$ or lower alkyl with hydrogen, halo, —CF$_3$ or —CH$_3$ being preferred, the phenyl ring contains 1, 2, or 3 X substituents and when there are 2 or 3 X substituents said substituents are the same or different;

Q is =O or —OH;

A is —N(R)— and B is —CH$_2$—, or A is —CH$_2$— and B is —N(R)—;

R is hydrogen, lower alkyl, lower alkanoyl, —CO$_2$R$^1$,

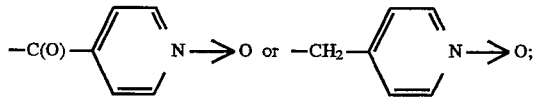

R$^1$ is hydrogen, lower alkyl or —CH$_2$CCl$_3$; and

— represents an optional double bond.

The invention also includes a pharmaceutical composition comprising a compound of formula XIV in combination with a pharmaceutically acceptable carrier, and a method of treating allergy or inflammation in a mammal which comprises administering an effective amount of a compound of formula XIV to a mammal in need of such treatment.

The compounds of this invention possess antihistaminic properties which may be assessed by the following in vitro test procedure for H$_1$ antihistamine activity.

ANTIHISTAMINE ACTIVITY ASSAY

In vitro assay: Ileal segments were removed from male Hartley guinea pigs (250–350 g) and suspended in 10 ml perfusion baths containing Tyrode's solution. The buffer was equilibrated with 95% O$_2$ and 5% CO$_2$ and maintained at a temperature of 37° C. The tissues were adjusted to 0.5–1 g tension and allowed to equilibrate for 30 min. All responses were recorded isometrically by means of a Grasse smooth muscle transducer and electronic recorder. Drugs were tested for their ability to inhibit the spasmogenic activity of histamine dihydrochloride. Two cumulative control log concentration-response curves for histamine (10$^{-7}$–10$^{-5}$M) were generated for each tissue. Antagonists were added to the bath and allowed to act for 5 min. before another histamine curve was generated.

Drugs were evaluated for their ability to inhibit histamine and thereby shift the response curve to the right. From this data, Ki (dissociation constant of the antagonists with the receptor) and pA$_2$ (negative log of the molar concentration of the inhibitor which would require that twice as much agonist be used to elicit a chosen response) values were determined. These values were used to determine relative potency.

The compounds of the invention also possess platelet-activating factor (PAF) antagonistic properties. The compounds of the invention are therefore useful whenever PAF is a factor in the disease or disorder. This includes allergic diseases such as asthma, adult respiratory distress syndrome, urticaria and inflammatory diseases such as rheumatoid arthritis and osteoarthritis.

The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF. The in vitro assay is a simple screening test, while the in vivo test mimics clinical use of PAF antagonists to provide data which simulates clinical use of the compounds described herein.

PAF ANTAGONISM ASSAY

In vitro Assay: Preparation of platelet-rich plasma (PRP): Human blood (50 ml) is collected from healthy male donors in an anticoagulant solution (5 ml) containing sodium citrate (3.8%) and dextrose (2%). Blood is centrifuged at 110 x g for 15 min. and the supernatant (PRP) carefully transferred into a polypropylene tube. Platelet-poor-plasma (PPP) is prepared by centrifuging PRP at 12,000 x g for 2 min. (Beckman Microfuge B). PRP is used within 3 hours of drawing the blood.

Platelet Aggregation Assay: When an aggregating agent such as PAF is added to PRP, platelets aggregate. The aggregation assays are performed using a dual-channel aggregometer (Model 440, Chrono-Log Corp., Havertown, Pa.). PRP (0.45 ml) in aggregometer cuvettes is continually stirred (37° C.). Solutions of test compounds or vehicle are added to the PRP, and after incubation for 2 min., 10–15 µl aliquots of PAF solution are added so as to achieve a final concentration of 1–5×10$^{-8}$M. Incubations are continued until the increase in light transmission reaches a maximum (usually 2 min). Values for inhibition are calculated by comparing maximal aggregation obtained in the absence and the presence of the compound. For each experiment, a standard PAF antagonist such as alprazolam is used as a positive internal control. The inhibitory concentration (IC$_{50}$) is the concentration of compound in micromoles at which 50% of the aggregation is inhibited, as measured by the light transmission through each sample of PRP as compared to PPP.

Compounds of the present invention are preferably administered in a pharmaceutical carrier suitable for oral or parenteral administration. Any convenient dosage form, such as capsules, tablets, powders, suspensions or solutions are contemplated. The pharmaceutical compositions or formulations can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily antihistaminic or anti-PAF dose of a compound of formula I for an average body weight of 70 kg is from about 0.25 to about 100 mg/kg of drug per day, preferably about 10 to about 20 mg/kg per day, given in single or 2–4 divided doses. The exact dose, however, is determined by the attending skilled clinician and is dependent in the potency of the compound administered, the age, weight, condition and response of the patient. The quantity of active compound in a unit dose may be varied from about 0.1 to about 500 mg, preferably from about 1 to about 100 mg.

The following examples of the preparation of compounds of formula I are intended to illustrate, but not to limit, the present invention.

EXAMPLE 1

Part A:

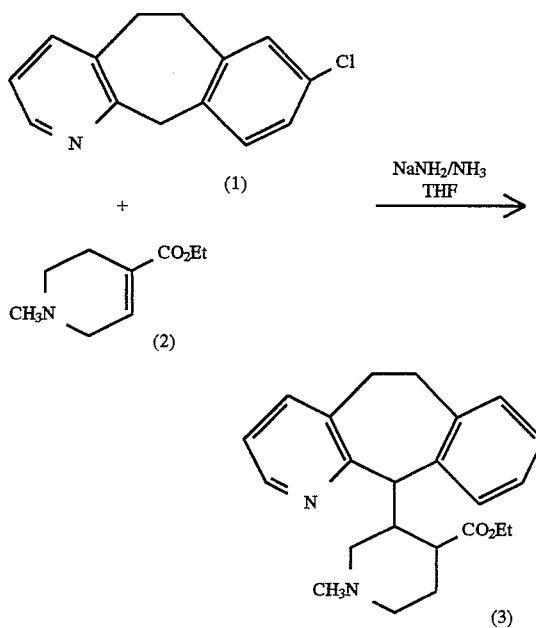

To a solution of NaNH₂ prepared from Na (0.85g), NH₃ (150 mL), and Fe(NO₃)₃·9H₂O (20 mg), add a solution of compound (1) (6.9 g) in THF (100 mL). After 45 min., add a solution of compound (2) (5.2 g) in Et₂O (50 mL). Stir the mixture for 18 h at room temperature, then pour into H₂O (200 mL). Separate the organic layer and extract the aqueous portion with EtOAc (2×150 mL). Dry the combined organic extracts over MgSO₄, filter and evaporate to an oil (10.6 g). Silica gel chromatography, eluting with 3% NEt₃/EtOAc, affords compound (3) (0.65 g).

Part B:

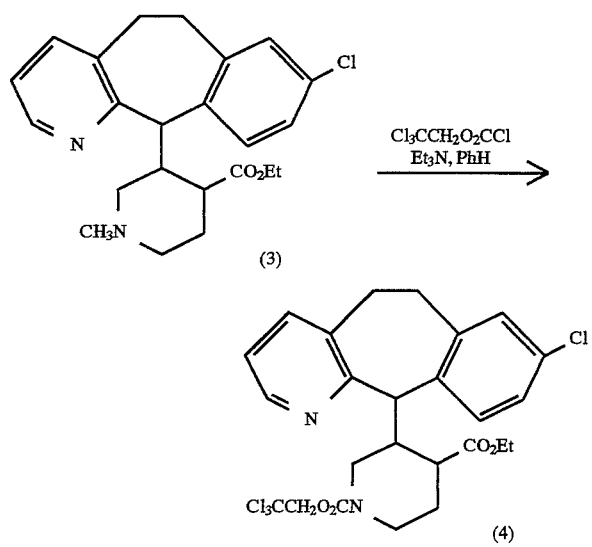

Heat compound (3) (0.65 g), Et₃N (0.2 g) and Cl₃CCH₂O₂CCl (0.4 g) in benzene (50 mL) at reflux temperature for 2 h. Add a second portion of Cl₃CCH₂O₂CCl (0.4 g) and continue refluxing for 2 h, then treat the reaction mixture with ice (20 g) and EtOAc (30 mL). Separate the organic layer and wash with dilute NH₄OH (20 mL) and with H₂O (2×20 mL). Extract the combined aqueous extracts with EtOAc (30 mL), combine the organic extracts, dry over MgSO₄, filter and evaporate to give an oil (1.2 g). Silica gel chromatography, eluting with 10–20% EtOAc/CH₂Cl₂, affords compound (4) (0.70 g). mp 168°–170° C.

Part C:

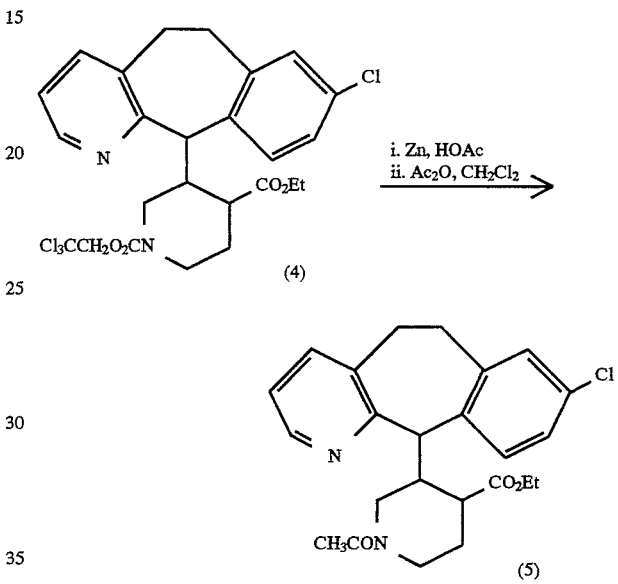

Heat compound (4) (0.68 g), Zn (1.2 g), and AcOH (10 mL) at 80°–100° C. under an N₂ atmosphere for 1 h. Filter the hot reaction mixture through a glass wool plug and rinse the residue with hot H₂O (3×10 mL) then CH₂Cl₂(2×10 mL). Cool the combined filtrates (external ice-bath) and adjust to basic pH by addition of concentrated NH₄OH. Separate the organic layer and extract the aqueous layer with CH₂Cl₂(2×20 mL). Combine the organic extracts, dry over MgSO₄, filter and evaporate to give an oil (0.5 g). Dissolve the oil in CH₂Cl₂(20 mL), treat with Ac₂O (1.0 g) and heat at reflux for 1 h under a N₂ atmosphere. Pour the reaction mixture onto ice (20 g), adjust to basic pH with concentrated NH₄OH, and separate the organic layer. Extract the aqueous layer with CH₂Cl₂(2×20 mL) and combine the organic extracts, dry over MgSO₄, filter and evaporate to give an oil (0.6 g). Silica gel chromatography, eluting with 2–6% NEt₃/EtOAc, affords compound (5) (0.44 g).

Part D:

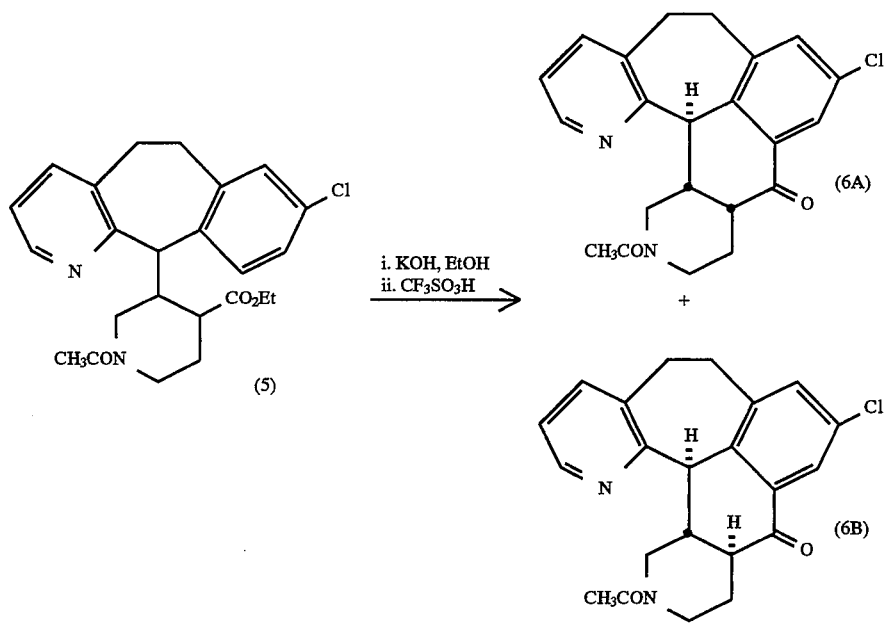

Stir compound (5) (0.32 g) and KOH (0.2 g) in EtOH at room temperature for 18 h, then add a second portion of KOH (0.2 g) and continue stirring for 24 h. Remove EtOH under reduced pressure and dissolve the residue in $H_2O$ (20 mL). Add concentrated HCl until pH 3.0 is attained and extract the solution with $CH_2Cl_2$ (3×20 mL). Combine the organic extracts, dry over $MgSO_4$, filter and evaporate to give a white foam (0.23 g). Dissolve the solid in triflic acid (10 mL), heat at 80°–100° C. for 2 h, then pour onto ice (20 g). Basify with concentrated $NH_4OH$ and extract with $CH_2Cl_2$ (3×20 mL). Combine the organic extracts, dry over $MgSO_4$, filter and evaporate to give an oil (0.22 g). Dissolve the oil in $CH_2Cl_2$ (20 mL), treat with $Ac_2O$ (1.0 mL) and heat at reflux for 1 h, then pour onto ice (20 g). Basify and extract as before, then combine the organic extracts, dry over $MgSO_4$, filter and evaporate to give an oil (0.20 g). Silica gel chromatography, eluting with 1.5–2.0% $MeOH/CH_2Cl_2$, gives compound (6), isomer A (0.06 g) (foam) and isomer B (0.02 g), mp 218°–220° C.

PART A:

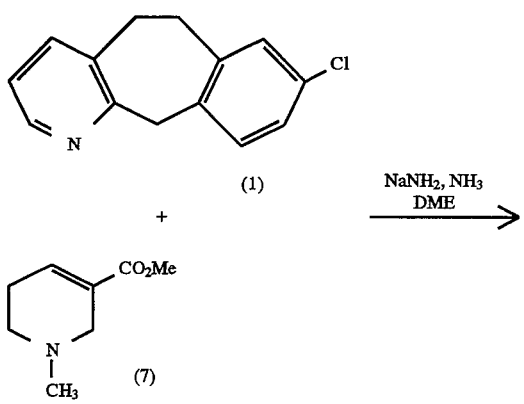

-continued

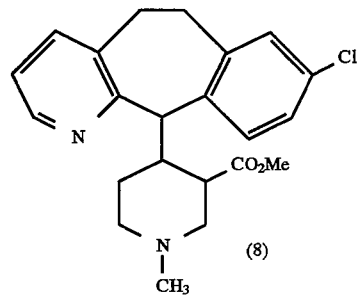

To a solution of $NaNH_2$, prepared from Na (1.20 g), $NH_3$ (150 mL), and $Fe(NO_3)_3.9H_2O$ (50 mg), add a solution of compound (1) (11.5 g) in 1,2-dimethoxyethane (DME) (150 mL) over 15 min, add a second portion of DME (150 mL) and evaporate the excess $NH_3$ by warming the reaction mixture to 40° C. Cool the reaction mixture to −78° C. (external $CO_2$/acetone bath) and add a solution of compound (7) (7.75 g) in DME (100 mL). Maintain the reaction mixture at −78° C. for 30 min, remove the cooling bath and treat the reaction mixture with $NH_4Cl$ (25 g) and saturated $NH_4Cl$ solution (125 mL). After stirring for 5 min, extract the solution with $Et_2O$ (300 mL). Wash the organic fraction with $H_2O$ (150 mL), combine the aqueous fractions and extract with $Et_2O$ (150 mL). Dry the combined organic fractions over $MgSO_4$, filter and evaporate to give an oil (21 g). Silica gel chromatography, eluting with 1.5–5.0% $NEt_3$/ EtOAc, gives compound (8) (12 g).

PART B:

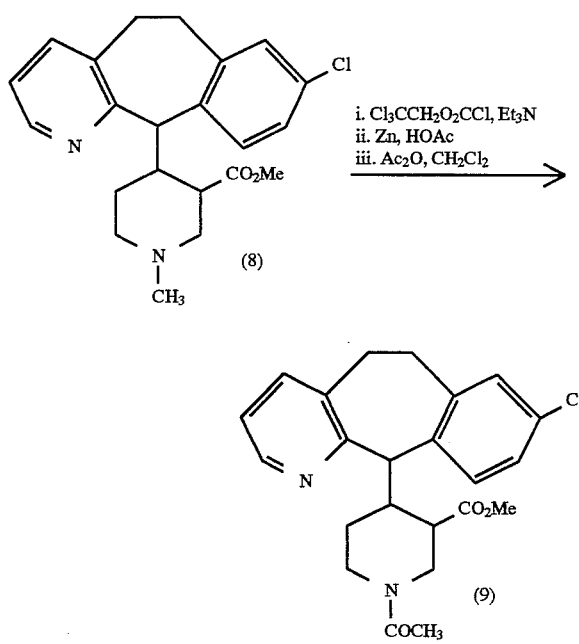

Heat compound (8) (1.1 g), triethylamine (0.4 g) and Cl₃CCH₂O₂CCl (0.5 g) in benzene (20 mL) at reflux temperature for 30 min. Add a second portion of Cl₃CCH₂O₂CCl (0.5 g), continue refluxing for 30 min, then treat the reaction mixture with ice (20 g) and basify with conc. NH₄OH. Extract the solution with EtOAc (40 mL), wash the extracts with H₂O (2×10 mL), dry over MgSO₄, filter and evaporate to give an oil (2.5 g). Silica gel chromatography, eluting with 5–30% EtOAc/CH₂Cl₂ gives a foam (1.4 g). Dissolve the foam in AcOH (15 mL), treat with Zn (2.1 g) and heat at 80°–100° C. for 1 h. Filter the reaction mixture and rinse the residue with hot H₂O (2×20 mL) then CH₂Cl₂ (2×20 mL). Cool the combined filtrates (external ice-bath) and basify with conc. NH₄OH. Separate the organic layer and extract the aqueous layer with CH₂Cl₂ (2×20 mL). Combine the organic extracts, dry over MgSO₄, filter and evaporate to give an oil (1.1 g). Dissolve the oil in CH₂Cl₂ (20 mL), treat with Ac₂O (1 mL) and heat at reflux for 1 h under an N₂ atmosphere. Pour the reaction mixture onto ice (20 g), adjust to basic pH with conc. NH₄OH and separate the organic layer. Extract the aqueous layer with CH₂Cl₂ (3×20 mL), combine the organic extracts, dry over MgSO₄, filter and evaporate to give an oil (1.2 g). Silica gel chromatography, eluting with 2.0–4.0% NEt₃/EtOAc, gives compound (9) (0.98 g) as a foam.

PART C:

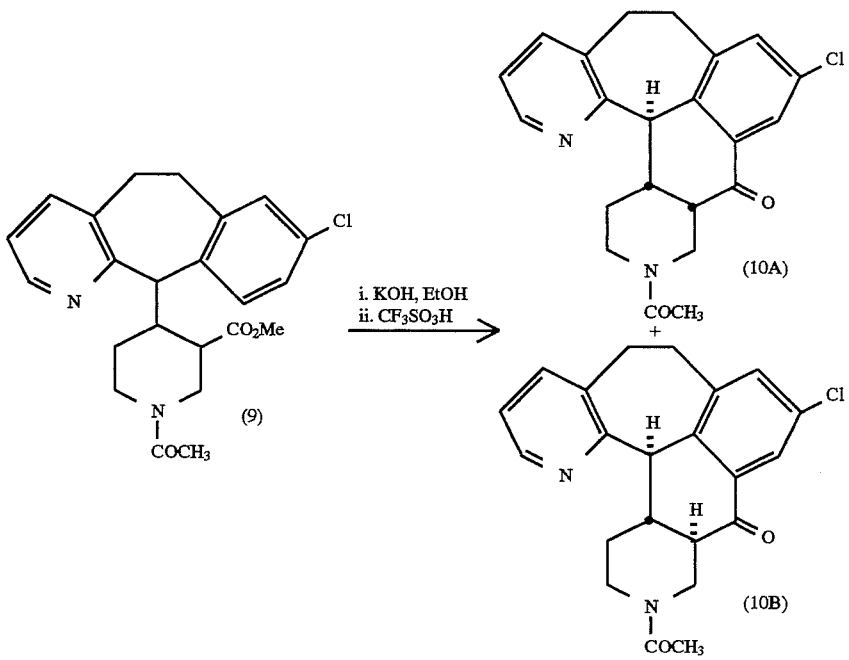

Stir compound (9) (0.96 g) and KOH (0.45 g) in EtOH (20 mL) at room temperature for 17 h, then add a second portion of KOH (0.5 g) and continue stirring for 24 h. Add Et$_2$O (30 mL) and extract the solution with H$_2$O (4×20 mL). Add conc. HCl to the aqueous solution until pH 3.0 is attained and extract the solution with CH$_2$Cl$_2$ (3×20 mL). Combine the organic extracts, dry over MgSO$_4$, filter and evaporate to give a foam (0.74 g). Dissolve the foam in triflic acid (20 mL), heat at 80°–85° C. for 2 h, then pour onto ice (20 g). Basify the solution with conc. NH$_4$OH and extract with CH$_2$Cl$_2$ (3×40 mL). Combine the organic extracts, dry over MgSO$_4$, filter and evaporate to give compound (10) (0.560 g).

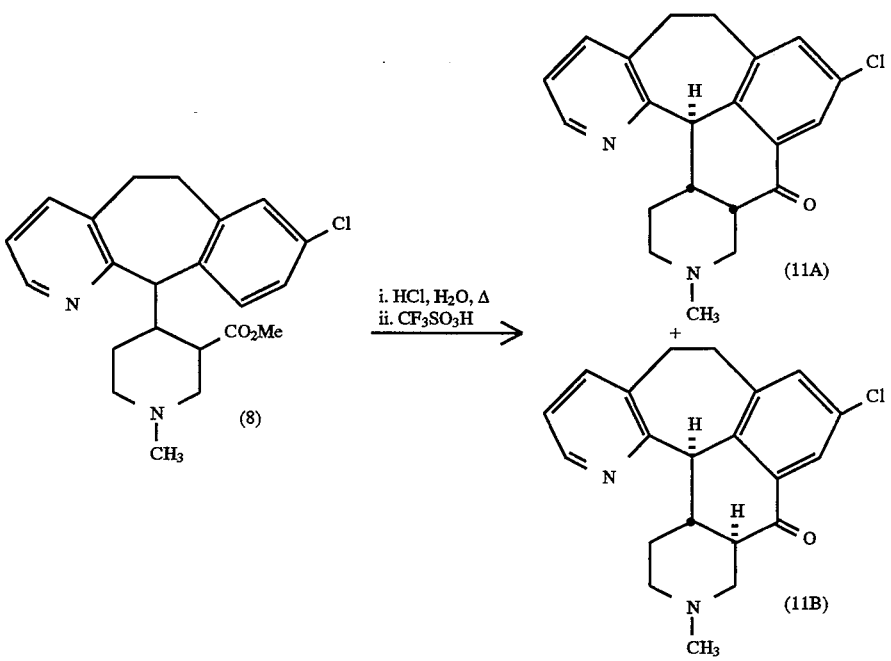

Reflux compound (8) (1.3 g) in concentrated HCl (15 mL) for 2 h, then evaporate the solution under high vacuum. Treat the residue with triflic acid (30 mL), stir at 90°–95° C. for 3 h, then pour onto ice. Basify with conc. NH$_4$OH and extract with CH$_2$Cl$_2$ (3×40 mL). Dry the organic extracts over MgSO$_4$, filter and evaporate to give an oil (1.2 g). Silica gel chromatography, eluting with 1.0–5.0% NEt$_3$/EtOAc, gives compound (11), isomer A (0.23 g), mp 220°–221° C. and isomer B (0.04 g), mp 209°–210° C.

PART A:

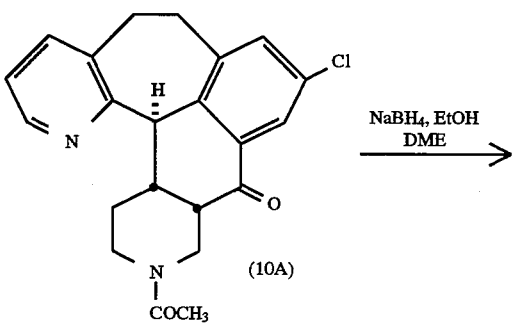

-continued

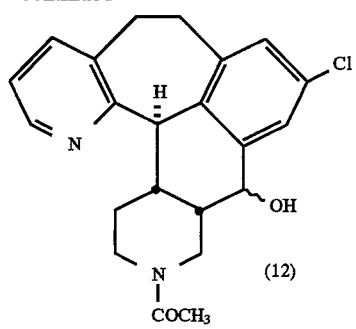

Treat compound (10A) (0.49 g) in DME (17 mL) and EtOH (18 mL) with NaBH$_4$ (0.3 g) and stir at room temperature for 24 h. Treat the reaction mixture with ice, extract with CH$_2$Cl$_2$ (3×30 mL), then combine the organic extracts, dry over MgSO$_4$, filter and evaporate to give compound (12) (0.38 g), mp 200°–210° C.

PART B:

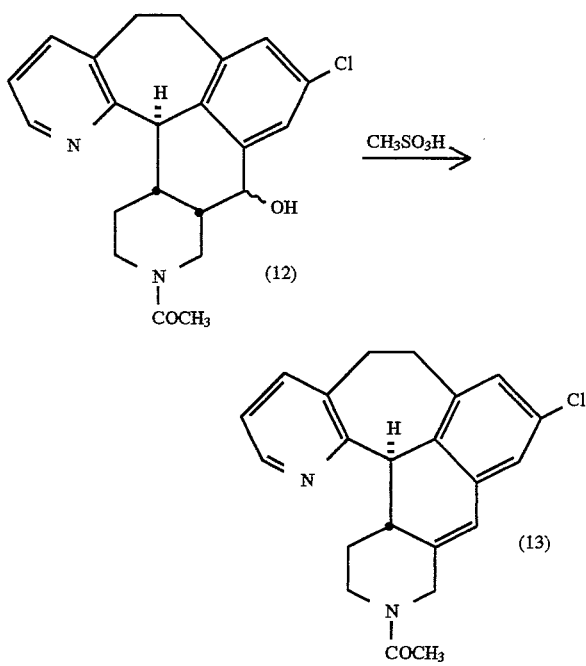

Treat compound (12) (0.82 g) with methanesulfonic acid (20 mL) and heat on a steam bath for 40 min. Pour the reaction mixture onto ice, basify the solution with conc. NH₄OH to obtain a white precipitate (0.78 g) and isolate it by filtration. Take up the solid in EtOAc (40 mL), wash with H₂O (10 mL), dry over MgSO₄, filter and evaporate to give compound (13) (0.75 g).

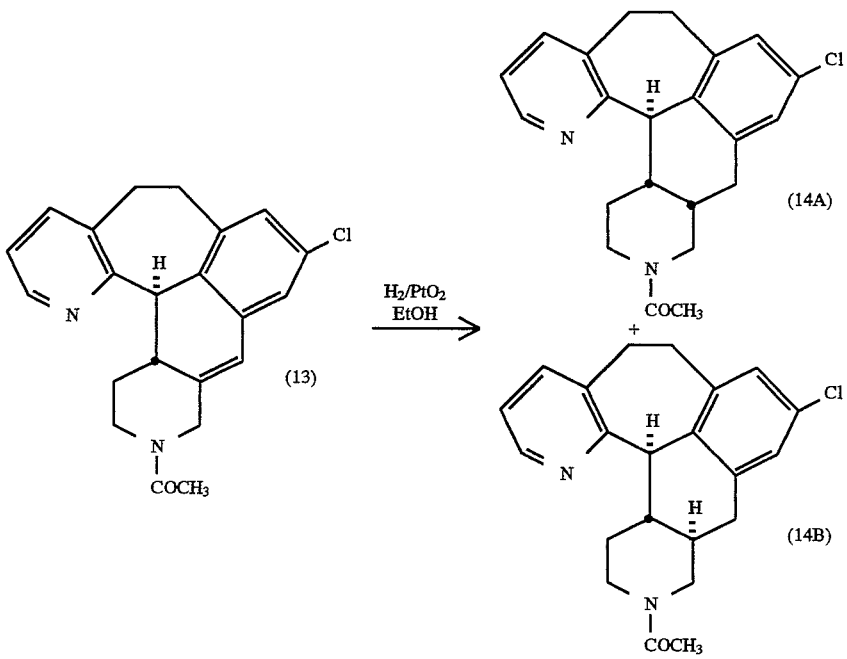

Treat compound (13) (0.5 g) in EtOH (20 mL) with PtO₂ and hydrogenate at 58 psi in a Parr hydrogenator for 5 h. Filter the reaction mixture and evaporate the filtrate to give a foam. Silica gel chromatography, eluting with 1.0–5.0% MeOH/CH₂Cl₂, gives compound (14), isomer A (0.05 g), and isomer B (0.09 g).

PART A:

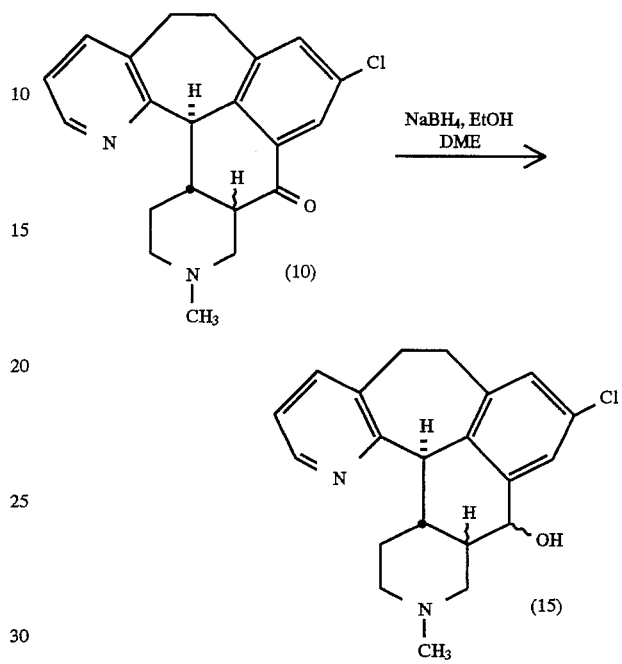

Treat compound (10) (0.5 g), in DME (20 mL) and EtOH (5 mL) with NaBH₄ (0.26 g) and stir at room temperature for 4 h. Pour the reaction mixture onto ice/H₂O (30 mL) and extract with CH₂Cl₂ (3×30 mL). Combine the organic extracts, dry over MgSO₄, filter and evaporate to give a gum (0.48 g). Silica gel chromatography, eluting with 0.5–3.0%

NEt₃/CH₂Cl₂, gives compound (15), isomer A (0.13 g) and isomer B (0.02 g).

PART B:

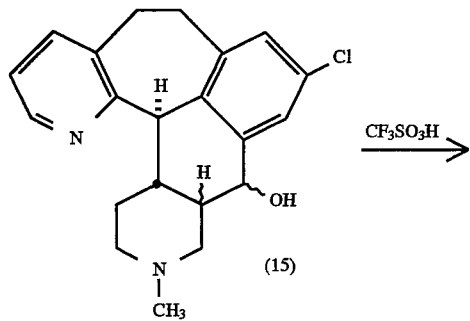

(15)

CF₃SO₃H →

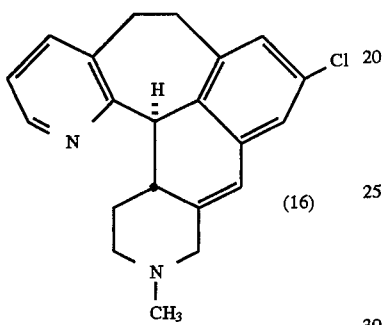

(16)

Heat compound (15) (0.13 g) in triflic acid (4 mL) on a steam bath for 30 min then pour onto ice and basify with conc. NH₄OH. Filter the solution, wash the solid residue with H₂O, then dissolve in CH₂Cl₂, dry over MgSO₄, filter and evaporate to give comppund (16) (0.10 g).

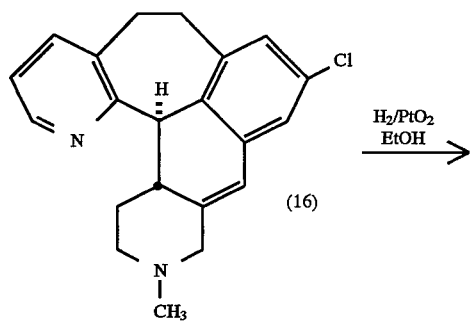

(16)

H₂/PtO₂
EtOH →

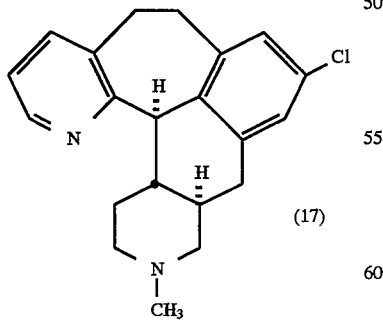

(17)

Treat compound (16) (3.5 g) in EtOH (75 mL) with PtO₂ (0.42 g) and hydrogenate in a Parr hydrogenator at 60 psi for 5 h, then add a further portion of PtO₂ (0.06 g) and hydrogenate for a further 17 h. Filter the reaction mixture and evaporate the filtrate. Redissolve the residue in MeOH, decolorize with Darco®, filter and evaporate to give a gum. Recrystallization from MeOH gives compound (17) (2.25 g), m.p. 180°–182° C.

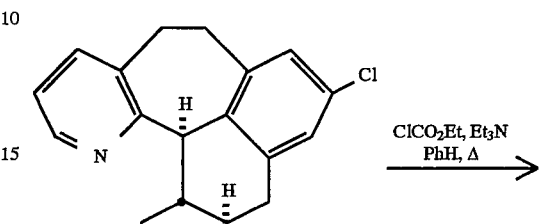

(17)

ClCO₂Et, Et₃N
PhH, Δ →

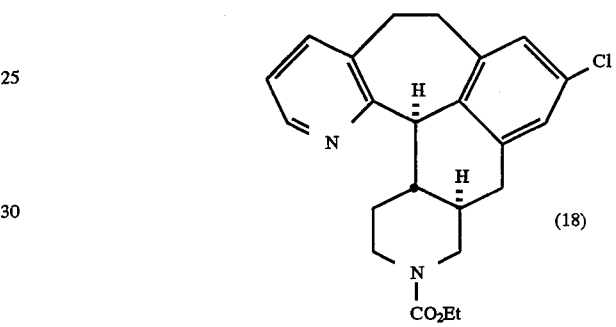

(18)

Treat compound (17) (0.50 g) in benzene (20 mL) with ClCO₂Et (0.32 g) and Et₃N (0.3 g) and heat at reflux for 2 h, add more ClCO₂Et (0.3 g) and Et₃N (0.3 g) and continue reflux for 30 min. Pour the reaction mixture onto ice and basify the solution with conc. NH₄OH. Extract the solution with EtOAc (2×30 mL), combine the organic fractions, dry over MgSO₄, filter and evaporate to give an oil (1.5 g). Recrystallization from Et₂O gives compound (18) (0.381 g), m.p.185°–187° C.

PARTS A and B:

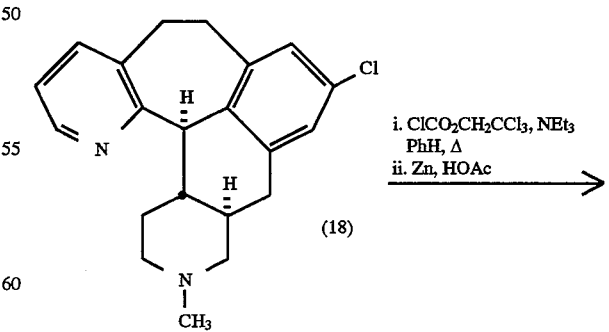

(17)  (18)

i. ClCO₂CH₂CCl₃, NEt₃
   PhH, Δ
ii. Zn, HOAc →

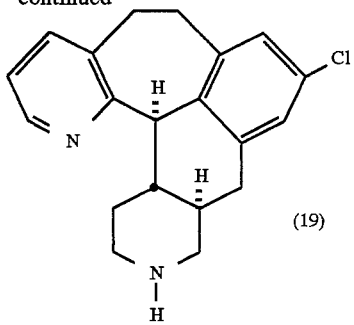

Treat compound (18) (0.50 g) in benzene (40 mL) with Et₃N (0.85 g) and ClCO₂CH₂CCl₃ (0.5 g) and heat at reflux for 1 h. Pour the reaction mixture onto ice and basify the solution with conc. NH₄OH. Extract the solution with Et₂O (30 mL), separate the organic fraction, wash with H₂O (20 mL), dry over MgSO₄, filter and evaporate. Dissolve the solid product (0.70 g) in AcOH (5 mL), treat with Zn (0.7 g) and heat at 80°–100° C. for 30 min. Filter the reaction mixture and rinse the residue with hot H₂O (2×20 mL). Basify the combined filtrates with concentrated NH₄OH and extract with CH₂Cl₂ (4×25 mL). Combine the organic extracts, dry over MgSO₄, filter and evaporate to give compound (19) (0.44 g).

PART C:

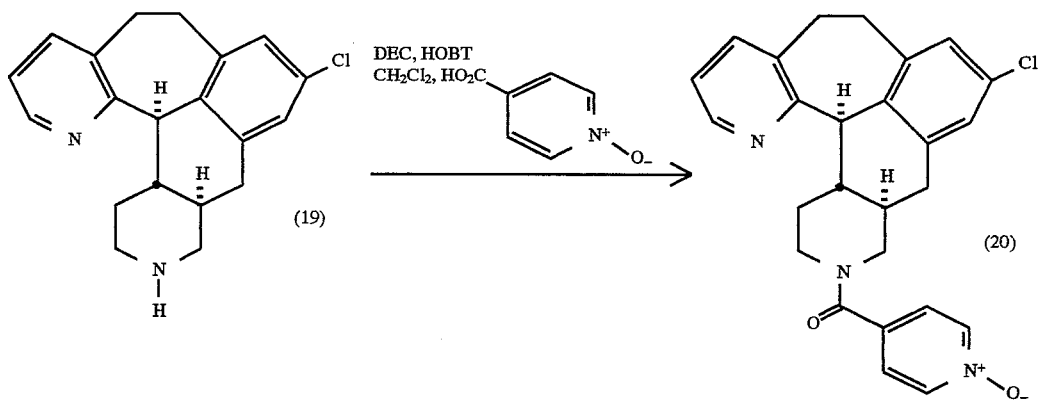

Dissolve compound (19) (0.34 g) in CH₂Cl₂ (50 mL) and treat sequentially with iso-nicotinic acid-N-oxide(0.16 g), N-hydroxybenzo-triazole (0.55 g) and 1-(3-dimethylaminopropyl)-3-ethyl carbodiimide HCl(0.22 g) while cooling the solution with an ice/NaCl/MeOH bath (external). Stir the reaction mixture and allow to warm to room temperature over 4 h. Treat the reaction mixture with 10% KH₂PO₄ solution (50 mL), stir for 15 min and separate the organic layer. Extract the aqueous fraction with CH₂Cl₂ (2×20 mL), dry the combined organic fractions over MgSO₄, filter and evaporate to give a solid (0.53 g). Silica gel chromatography, eluting with 1.0–4.0% MeOH/CH₂Cl₂, gives compound (20) (0.37 g).

The following formulations exemplify some of the dosage forms of this invention. In each, the term "active compound" designates a compound of formula I, preferably the compound of Example 7, i.e., 7-chloro-2,3,4,4a,5,9,10,14b,14c-decahydro-3-methylpyrido[2",3":7',6']-cyclohepta[1',2',3',:4,5]naphtho[2,3-c]pyridine.

EXAMPLE A

TABLETS

| No. | Ingredient | mg/tablet | mg/tablet |
|---|---|---|---|
| 1. | Active Compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix item nos. 1 and 2 in a suitable mixer for 10–15 minutes. Granulate the mixture with item no. 3. Mill the damp granules through a coarse screen (e.g., ¼") if needed. Dry the damp granules. Screen the dried granules if needed and mix with item no. 4 and mix for 10–15 minutes. Add item no. 5 and mix for 1–3 minutes. Compress the mixture to appropriate size and weight on a suitable tablet machine.

EXAMPLE B

Capsules

| No. | Ingredient | mg/capsule | mg/capsule |
|---|---|---|---|
| 1. | Active Compound | 100 | 500 |
| 2. | Lactose USP | 106 | 123 |
| 3. | Corn Starch, Food Grade, | 40 | 70 |
| 4. | Magnesium Stearate NF | 4 | 7 |
| | Total | 250 | 700 |

Method of Manufacture

Mix item nos. 1, 2 and 3 in a suitable blender for 10–15 minutes. Add item no. 4 and mix for 1–3 minutes. Fill the mixture into suitable two-piece hard gelatin capsules on a suitable encapsulating machine.

Using the antihistamine activity assay test procedure described above, the compound of Example 7 was found to have a dissociation constant (Ki) of 1.0 and a pA₂ of 8.85.

Using the PAF antagonism assay described above, the following results were obtained for compounds identified below by Example and compound number:

| Ex. | Cpd. | Inhibition of PAF-induced platelet aggregation |
|---|---|---|
| 1 | 6A | 33% at 50 μM |
| 1 | 6B | 49% at 50 μM |
| 2 | 10A | 15% at 50 μM |
| 3 | 11A | 47% at 50 μM |
| 3 | 11B | 4% at 50 μM |
| 4 | 13 | 23% at 50 μM |
| 5 | 14A | IC₅₀ ≅ 3000 μM |
| 5 | 14B | IC₅₀ ≅ 300 μM |
| 6 | 16 | IC₅₀ ≅ 5.5 μM |
| 7 | 17 | IC₅₀ ≅ 38 μM |
| 9 | 20 | IC₅₀ ≅ 2.8 μM |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound represented by the structural formula

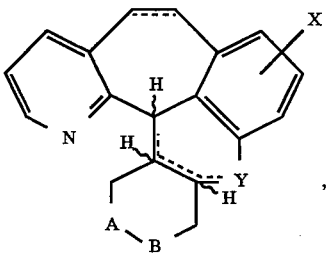

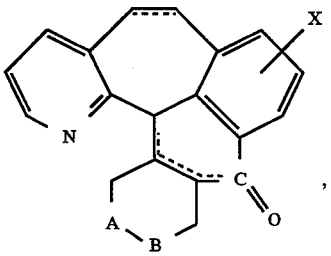 Ia

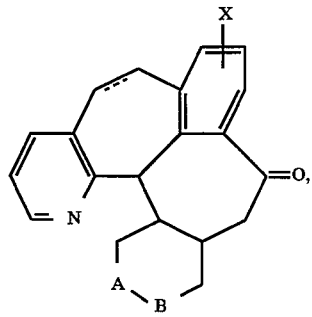 Ic

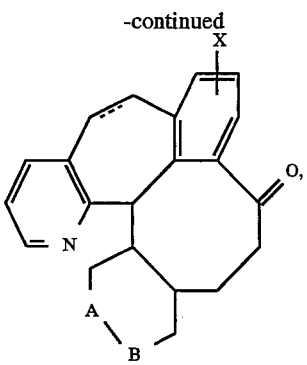 Ic'

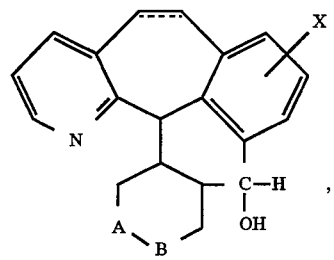 Ia' or a pharmaceutically acceptable salt thereof, wherein

X is hydrogen, halo, —CF₃ or —CH₃—;

Y is —(CH₂)ₙ—, wherein n is 1, 2 or 3;

A is —N(R)— and B is —CH₂—, or A is —CH₂— and B is —N(R)—;

R is hydrogen, lower alkyl, lower alkanoyl, —CO₂R¹,

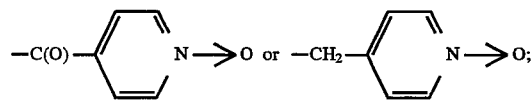

R¹ is hydrogen, lower alkyl or —CH₂CCl₃; and

- - - - represents an optional double bond, with the proviso that the ring containing Y has only one optional double bond.

2. The compound of claim 1 having the formula:

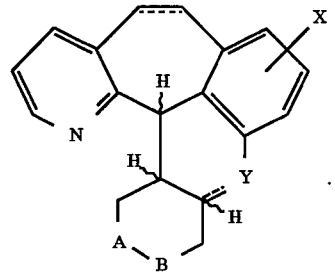 Ii

3. The compound of claim 1 having the formula:

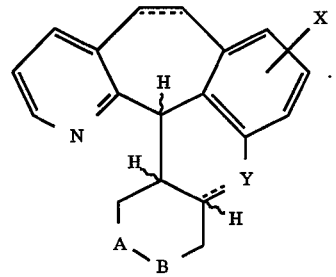 Ii

4. A compound of claim 1 wherein said compound is

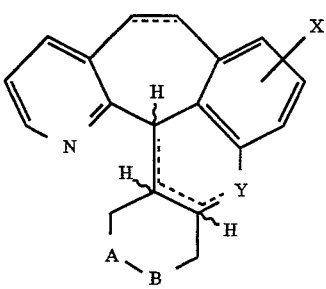

wherein Y is —(CH$_2$)$_n$— wherein n is 1, or =CH—, or said compound is

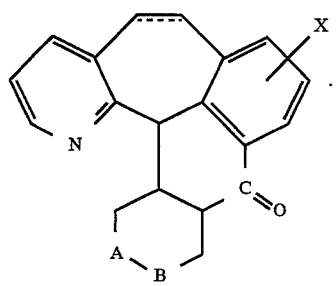

5. A compound of claim 1 wherein A is —CH$_2$— and B is —N(R)—.

6. A compound of claim 1 wherein R is lower alkyl, acetyl, ethyl carboxylate or pyridylcarbonyl N-oxide.

7. A compound of claim 1 wherein X is chloro.

8. A compound of claim 1 wherein said compound is

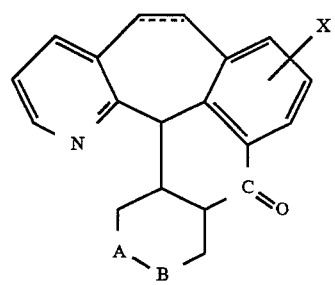

or

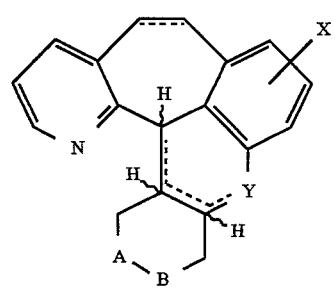

wherein Y is —(CH$_2$)$_n$— wherein n is 1, or =CH—; X is chloro; A is —CH$_2$—; B is —N(R)—; and R is lower alkyl, acetyl, ethyl carboxylate or pyridylcarbonyl N-oxide.

9. A compound of claim 1 selected from the group consisting of compounds represented by the following structural formulae:

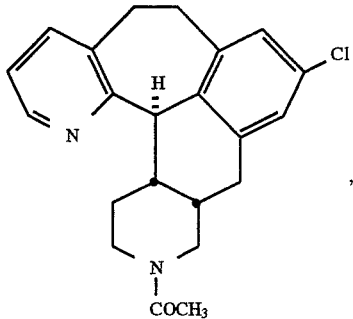

,

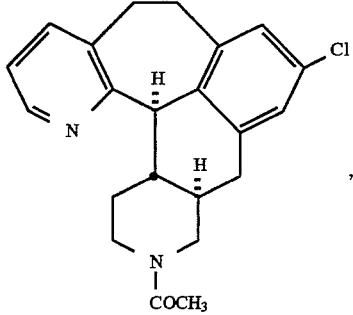

,

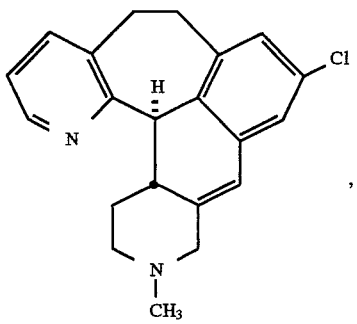

,

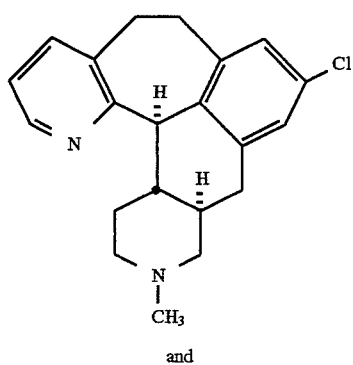

and

-continued
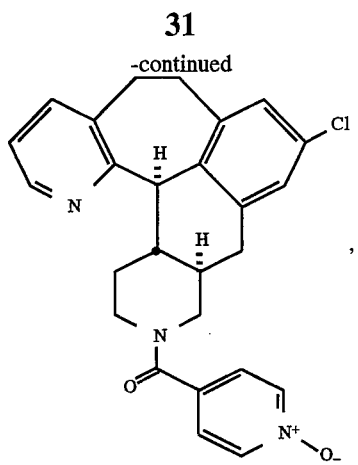
,
10. A pharmaceutical composition comprising a compound of claim 1 in a pharmaceutically acceptable carrier, wherein the quantity of said compound in a unit dose is about 0.1 to about 500 mg.
11. A method of treating allergy or inflammation comprising administering a pharmaceutical composition of claim 10 to a mammal in need of such treatment.
* * * * *